United States Patent [19]

Barabe

[11] Patent Number: 4,741,700
[45] Date of Patent: May 3, 1988

[54] DENTAL BREATH FRESHENING DEVICE

[76] Inventor: David J. Barabe, 2741 Lansdale La., Winston-Salem, N.C. 27103

[21] Appl. No.: 886,636

[22] Filed: Jul. 16, 1986

[51] Int. Cl.⁴ .............................................. A61C 5/00
[52] U.S. Cl. .................................... 433/229; 433/215
[58] Field of Search ............... 433/229, 215; 604/890, 604/891, 57, 77, 307, 892

[56] References Cited

U.S. PATENT DOCUMENTS

| 2,835,628 | 5/1958 | Saffir | 433/229 |
| 2,930,128 | 3/1960 | Berens | 433/138 |
| 3,153,855 | 10/1964 | Holland | 433/202.1 |
| 3,503,127 | 3/1970 | Kasdin et al. | 433/199.1 |
| 3,600,807 | 8/1971 | Sipos | 433/229 |
| 4,464,114 | 8/1984 | Anthony | 433/229 |
| 4,533,326 | 8/1985 | Anthony | 433/229 |

FOREIGN PATENT DOCUMENTS

| 2247736 | 4/1974 | Fed. Rep. of Germany | 433/229 |
| 7425254 | 2/1976 | France | 433/229 |
| 86/00213 | 1/1986 | PCT Int'l Appl. | 433/229 |

OTHER PUBLICATIONS

"Gum Disease Alleviated by Pellets", by Patricia E. Raber, *Dentistry Today*, vo. 5, No. 5, Jun., 1986, pp. 1 and 22.

*Primary Examiner*—John J. Wilson
*Assistant Examiner*—Michael Lynch
*Attorney, Agent, or Firm*—Richard E. Jenkins

[57] ABSTRACT

A dental breath freshening device for rendering the mouth cavity pleasantly tasteful and freshening the breath. The device is adapted to be secured to a natural tooth and includes a long-lasting, soluble aromatic mint which is activated by saliva flow thereover in order to freshen the breath of the user for an extended period of time.

14 Claims, 3 Drawing Sheets

DENTAL BREATH FRESHENING DEVICE

TECHNICAL FIELD

This invention relates to breath fresheners and more particularly to a dental breath freshener device adapted to be secured to a tooth in the mouth of a person in order to provide long term relief from halitosis or bad breath.

BACKGROUND ART

The problems associated with bad breath are well known to people of all ages, but are of particular concern to young people. It is a relatively common sight to see teenagers chewing gum and breath mints when they are in the presence of their friends in order to assure a fresh breath and obviate the possibility of unpleasant bad breath. This phenomenon can also be observed by others in situations such as at church where one can observe people chewing gum or mints after the service in order to assure a fresh impression when they speak to their friends. However, gum and conventional breath mints produce only a very short-lived result of perhaps about 15 to 30 minutes. Moreover, chewing gum typically produces an unsightly impression when being chewed and is awkward to attempt to manipulate while one is talking. Thus, the search for a more perfect dental breath freshener which does not possess the shortcomings of the aforementioned gum and mints has continued, and a widely acceptable alternative has not as yet been developed to fill this long felt need by people who are conscientious of the impression they make upon their friends, relatives and acquaintances.

DISCLOSURE OF THE INVENTION

Accordingly, there is a need for a dental breath freshening device for use by people, particularly younger people, which is simple to use and long-lasting in its effect. Applicant believes that the present invention provides such a device. In accordance with the present invention, a dental breath freshening device has been discovered which may be easily secured to a selected tooth within the mouth of a user and provides long term breath freshening effect. The device comprises a base which is adapted to be secured to the surface of a tooth, preferably the first or second permanent molar so as to be adjacent to the parodid duct (major saliva gland), to assure a constant flow of saliva over the breath freshening device. The device further comprises a saliva soluble aromatic mint which is attached to the base to provide a long-lasting breath freshening effect of at least four hours or more.

Several embodiments of the breath freshening device are contemplated which include two embodiments wherein the device is bonded to a molar by a dentist and the user thereafter attaches slow dissolving aromatic mints thereto at a selected time and place in order to assure long-lasting fresh breath. A third embodiment of the present invention contemplates a breath freshening device having its own adhesive which is adapted to be secured by the user to a selected site on a molar tooth. When the long-lasting soluble aromatic mint portion of the device has fully been dissolved by saliva, the user will remove the device from the molar and replace it with another as needed.

The present invention may be carried out in several different forms, three of which will be described in more detail hereafter.

An object of this invention is to provide a long-lasting dental breath freshening device which is secured to a tooth of the user so that oral cavity saliva will naturally dissolve the aromatic mint portion thereof and assure fresh breath for an extended period of time.

Another object of the invention is to provide a simple and long-lasting breath freshening device for teenagers and other young people who are very sensitive about their breath and the impression which they make with their friends and members of the opposite sex.

Still another object of the invention is to provide a long-lasting dental breath freshening device which will obviate the need for the use of breath mints and unsightly chewing gum, and the short term effects achieved thereby, by people who are conscientious of the impression which they make on others.

Some of the objects of the invention having been stated, other objects will become evident as the description proceeds when taken in connection with the accompanying drawings.

BEST MODE FOR CARRYING OUT THE INVENTION

Figure 1:
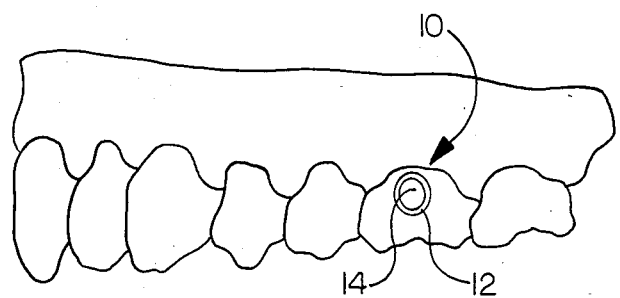
FIG. 1 is a side elevation view of the upper jaw and the breath freshening device illustrating an embodiment in accordance with the principles of the present invention.

Referring now to the drawings, and in particular to FIG. 1, there is illustrated an upper jaw and the teeth secured therein. The dental breath freshening device, generally designated 10, is shown as affixed to the outwardly facing surface of the second permanent molar tooth located beneath the parodid duct which is one of the major saliva glands of the mouth. This particular location of breath freshening device 10 assures that it will be constantly provided with a natural flow of saliva thereover in order to assure its proper functioning. It should be appreciated that breath freshening device 10 is affixed to the tooth using a now common dental technique called "bonding" wherein breath freshening device 10 is directly attached to the tooth with a very strong glue. This requires the assistance of a dentist or other dental professional in order to initially secure breath freshening device 10 to the proper site in the mouth of the user. Thereafter, dental breath freshening device 10 may be attended to and cleaned by the user without any further servicing by the dentist until removal thereof may be desired.

Figure 2:
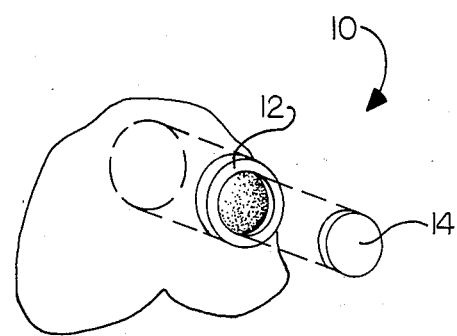
FIG. 2 is a perspective view of the embodiment of FIG. 1 exploded from the tooth for clarity of explanation.
Figure 3:
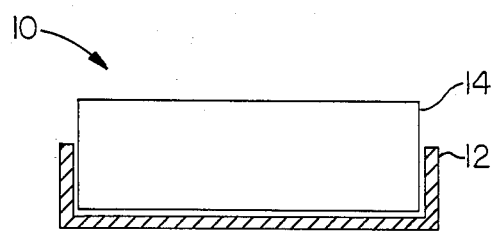
FIG. 3 is a vertical cross-sectional view of the embodiment of FIG. 1.

Dental breath freshening device 10, as best seen in FIGS. 2 and 3, comprises a base receptacle 12 and a suitable slow dissolving aromatic breath mint 14. Receptacle 12 may be of any suitable construction but as illustrated herein comprises a cup-like design having a flat base portion with an outwardly extending lip around the periphery thereof so as to define a receptacle for receiving and retaining mint 14. Although receptacle 12 may be fabricated from any suitably long-lasting and rigid material, it is presently contemplated that a metallic substance may be most suitable. Once receptacle 12 has been bonded to a selected site on the tooth of a user, it is ready to be utilized to receive and engage mints 14 placed therein by the user. Mint 14 may be constructed of any suitable slow release, soluble aromatic compound which is not detrimental to the teeth and skin tissue of the user's mouth. Mint 14 will most preferably have a total dissolution time of 4, 8 or 12 hours according to the particular mint inserted by the user into receptacle 12.

Figure 4:
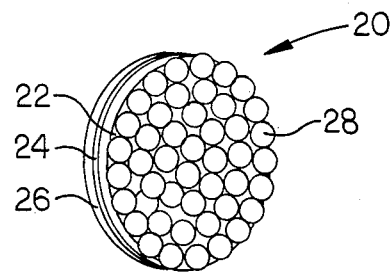
FIG. 4 is a perspective view of another embodiment in accordance with the principles of the present invention.
Figure 5:
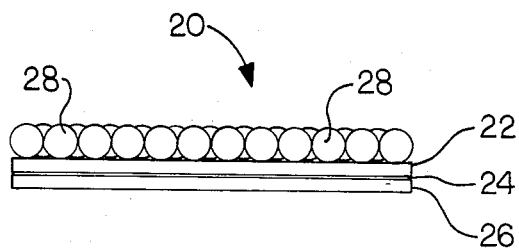
FIG. 5 is a side elevation view of the embodiment of FIG. 4.

With reference now to FIGS. 4 and 5, a second embodiment of the breath freshening device is shown which may be affixed to a selected tooth by the user himself without the necessity of obtaining the services of a dentist or dental professional. Breath freshening device 20 comprises a base 22 having an adhesive composition 24 on the bottom surface thereof and, most suitably, a removable protective cover 26 over adhesive composition 24. Although the long-lasting soluble aromatic substance utilized in device 20 is matter of design choice, a plurality of timed release micro-pellets 28 are illustrated in FIGS. 4 and 5. Micro-pellets 28 are adhesively affixed to base 22 with a suitable water insoluble glue (not shown). Therefore, breath freshening device 20 may be affixed by the user to a tooth in his mouth, preferably the second molar, at a time and place of his choice in order to be assured of prolonged breath freshness. When micro-pellets 28 have fully dissolved and device 20 has served its purpose, it may be easily removed by the user and remaining base 22 and the adhesive composition 24 on the bottom thereof properly disposed of. This particular embodiment of the invention is very attractive in view of the ability of the user to affix it to one of his teeth without the aid of a dentist and to then remove it in its entirety when micro-pellets 28 are fully dissolved after an extended period of time.

The glue 24 used to attach breath freshening device 20 to the selected tooth is a natural superglue which is impervious to water and found in mussels. The mussel glue is new and understood to be available from Bio-Polymers, Inc. of Farmington, Conn. and is the preferred adhesive composition for use in the second embodiment of the present invention although others may be utilized as necessary.

Figure 6:
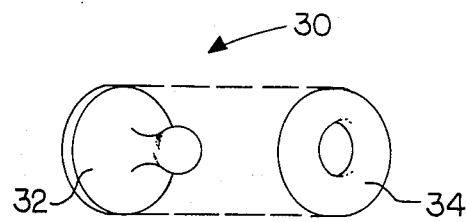
FIG. 6 is an exploded view of still another embodiment in accordance with the principles of the present invention.
Figure 7:
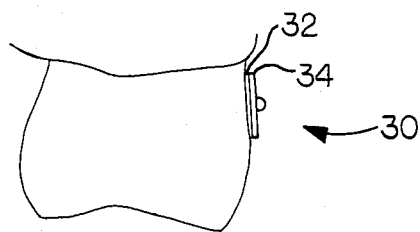
FIG. 7 is a front elevation view of the embodiment of FIG. 6 affixed to a tooth.

A third embodiment of the breath freshening device is illustrated in FIGS. 6 and 7 and is generally designated 30. Breath freshening device 30 is similar to the first embodiment described hereinabove and comprises base 32, which is bonded by a dentist to a selected molar, and doughnut-shaped breath mint 34. Base element 32 is most suitably constructed of substantially rigid Nylon and includes a projection extending outwardly therefrom over which a mint 34 is snugly attached as needed by the user for prolonged breath protection. The projection or "knob" extending from base 32 serves as a guide to facilitate placement of mint 34 thereon by the user of the present invention.

Although not specifically noted above, it should also be appreciated that soluble vitamins or medicinal compositions may be substituted for the aromatic mints and micro-pellets utilized in the instant invention. In this fashion, timed-release of a desired vitamin or medicine into the user's body may be easily accomplished.

It will be understood that various details of the invention may be changed without departing from the scope of the invention. Furthermore, the foregoing description is for the purpose of illustration only and not for the purpose of limitation—the invention being defined by the claims.

What is claimed is:

1. A breath freshening device for attachment to a natural tooth within the mouth of a user comprising:
    a base means having means for bonding said base means to the surface of the natural tooth; and
    a soluble aromatic substance replaceably engaged by said base means, whereby saliva can flow over and dissolve said aromatic substance and thereby freshen the breath of the user for an extended period of time.

2. A breath freshening device according to claim 1 wherein said base means comprises a generally rigid receptacle having an open portion therein for removably engaging said aromatic substance.

3. A breath freshening device according to claim 1 wherein said base means comprises a generally rigid base having a projection extending outwardly therefrom for removably engaging said aromatic substance.

4. A breath freshening device according to claim 2 or 3 wherein said base means is adapted to be bonded to the tooth surface using professional dental bonding.

5. A breath freshening device according to claim 1 wherein said aromatic substance is a slowly dissolvable breath mint which requires at least 4 hours to be dissolved by saliva flow within the mouth of the user.

6. A breath freshening device for attachment to a natural tooth within the mouth of a user comprising a generally flat base having an adhesive on one side thereof and a slow dissolving aromatic breath mint secured to the other side thereof, whereby said device may be attached to the tooth by the user and the user's breath freshened for an extended period of time by natural saliva flow over said breath mint.

7. A breath freshening device according to claim 6 wherein said adhesive is a glue derived from mussels.

8. A breath freshening device for attachment to a natural tooth within the mouth of a user comprising a receptacle defining an open portion therein and having means for bonding said receptacle to the surface of the natural tooth of the user, and a slow dissolving aromatic breath mint replaceably positioned in said open portion of said receptacle, whereby saliva can flow over and dissolve said aromatic mint and thereby freshen the breath of the user for an extended time.

9. A breath freshening device for attachment to a natural tooth within the mouth of a user comprising a base having a projection extending outwardly therefrom and having means for bonding said base to the natural tooth of the user, and a slow dissolving aromatic breath mint defining an aperture therein replaceably positioned on said projection, whereby saliva can flow over and dissolve said aromatic mint and thereby freshen the breath of the user for an extended time.

10. A device for attachment to a natural tooth within the mouth of a user comprising:

a base means having means for bonding said base means to the surface of the natural tooth; and a soluble substance replaceably engaged by said base means, whereby saliva can flow over and dissolve said soluble substance during a predetermined period of time.

11. A device according to claim 10 wherein said soluble substance comprises a medication.

12. A device according to claim 10 wherein said soluble substance comprises a vitamin.

13. A breath freshening device for attachment to a natural tooth within the mouth of a user comprising:

a generally flat base having an adhesive on one side thereof to facilitate affixation to the surface of the natural tooth by the user; and a soluble aromatic substance adhered to the other side of said base, whereby saliva can flow over and dissolve said aromatic substance and thereby freshen the breath of the user for an extended period of time.

14. A breath freshening device according to claim 13 wherein said aromatic substance comprises a slowly dissolvable breath mint which requires at least four hours to be dissolved by saliva flow within the mouth of the user.

* * * * *